(12) United States Patent
Jakob et al.

(10) Patent No.: US 6,319,288 B1
(45) Date of Patent: *Nov. 20, 2001

(54) FORMAMIDINESULFINIC-ACID COMPOSITIONS

(75) Inventors: Harald Jakob, Hasselroth; Bernd Hopf, Karlstein, both of (DE)

(73) Assignee: Degussa AG, Hanau (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/314,008

(22) Filed: May 19, 1999

(30) Foreign Application Priority Data

May 20, 1998 (DE) ............................. 198 22 597
Jul. 25, 1998 (DE) ............................. 198 33 629
Nov. 18, 1998 (DE) ............................. 198 53 122

(51) Int. Cl.$^7$ ..................... D06L 3/10; D21C 9/10
(52) U.S. Cl. .................. 8/110; 252/188.2; 8/107; 8/101; 8/125; 162/72
(58) Field of Search ................... 8/101, 102, 107, 8/110; 252/188.1–188.24; 162/72

(56) References Cited

U.S. PATENT DOCUMENTS

| 4,197,256 | 4/1980 | Sato et al. ............... 260/513.7 |
| 4,244,780 | 1/1981 | Rende ............................ 162/72 |
| 5,549,715 | * 8/1996 | Olip . | |

FOREIGN PATENT DOCUMENTS 0824145   2/1998   (EP) .

OTHER PUBLICATIONS

Database WPI Section Ch. Week 9226, Derwent Publications Class E16, An 92–214279 XP002110820, JP 04 145064, May 19, 1992.

Database WPI Section Ch. Week 8921, Derwent Publications Class D25, An 89–155167 XP002110821, JP 01 096298, Apr. 14, 1989.

Database WPI Section Ch. Week 9442, Derwent Publications Class A60, An 94–338256 XP002110822, JP 06 263721, Sep. 20, 1994.

* cited by examiner

*Primary Examiner*—Margaret Einsmann
(74) *Attorney, Agent, or Firm*—Smith, Gambrell & Russell, LLP

(57) ABSTRACT

A blend is disclosed containing formamidinesulfinic acid, an scale-inhibiting agent that can be neutral or acidic, and/or finely divided silica having good flowability to be used for the purpose of reductive bleaching in the paper and textile industries, whereby, in particular, polcarboxylates and polyacrylic acids are employed having a content of about 10% of a polyamide in the form of a copolymer.

11 Claims, No Drawings

FORMAMIDINESULFINIC-ACID COMPOSITIONS

INTRODUCTION AND BACKGROUND

The present invention relates to pulverulent or granulated blends that contain formamidinesulfinic acid (FAS), at least one anti-coating agent and/or finely divided silicic acid.

Formamidinesulfinic acid (FAS) is employed in the form of an aqueous alkaline solution for the purpose of reductive bleaching in the paper and textile industries. Whereas FAS is relatively sparingly soluble in water (about 27 g/l), under alkaline conditions up to 100 g/l FAS goes into solution as sulfinate. For the bleaching liquor the optimal quantitative ratio of FAS to lye (NaOH, $Na_2CO_3$) amounts to around 2:1. It is a disadvantage that the salts of formamidinesulfinic acid rapidly decompose in aqueous solution. Alkaline bleaching solutions are therefore produced in the paper industry only a short time before being added in metered amounts, and they then have to be consumed as quickly as possible.

For the continuous production and metering of bleaching solutions consisting of FAS and NaOH a special metering system has been conceived, which is in service with the majority of FAS customers. These systems run for 24 hours a day (as needed, during the working season or non-stop for several months). Manpower for constantly monitoring this metering of FAS is not available, or is only available to a very limited extent. Whereas addition of the alkaline FAS bleaching solution functions well in the case of the metering system that operates continuously, the metering of FAS causes operational problems again and again: FAS cakes together in the feed hopper (shaft) and does not slide, resulting in diminished addition and also in compaction of FAS in the region of the screw. At the present time the incorporation of vibrators or pneumatic beaters in the shaft is intended to provide a remedy. By virtue of the fluctuating flowability/grain-quality, fluctuating metered amounts often occur at constant screw speed.

The storage of FAS also causes difficulties quite often, since FAS possesses only low thermal stability. For instance, the SADT (self-accelerating decomposition temperature) ranges at around 50° C. Since, depending on storage conditions, temperatures clearly above 30 degrees have to be reckoned with again and again, problems with stability in storage occur in such cases. After just a few months a distinct decline in flowability occurs, proceeding as far as agglomeration (FAS is weakly hygroscopic), a yellow coloration and also an increase in the thiourea content. The latter is of particular significance if the limit of 0.1% thiourea (TU), which in many countries is subject to mandatory labelling, is exceeded.

Although many stabilizing agents that are current in the industry improve the thermal stability of FAS, they cannot be admixed, since they give rise to an unpleasant odour similar to that of hydrogen sulfide. Besides the poor flowability, in particular lime deposits in dissolving vessels and pipelines pertaining to FAS metering lines represent a problem. Due to the high pH value of the FAS bleaching solutions, current scale-inhibitors generally display a limited effect.

With a view to eliminating the lime deposits, the systems have to be switched off, flushed with mineral acids and cleaned.

An object of the present invention is to make available an FAS that remains flowable also in the event of storage and that prevents the formation of lime deposits in the course of its use. At the same time, it is an objective to increase the stability in storage as a result of stabilization of the FAS.

SUMMARY OF THE INVENTION

The above and other objects can be achieved according to the invention by a blend that comprises FAS, an anti-coating agent (pulverulent or granulated) with a preferably acidic or neutral pH value, and/or a finely divided, preferably precipitated, hydrophilic silica.

It is also possible, however, to employ silica that have been made water-repellent.

Stabilization of the FAS occurs readily if the silica has been mixed in on its own. If the blend contains the anti-coating agent and silica, a previously produced mixture of anti-coating agent and silica is advantageously added in the desired concentration ratios.

The silica is generally admixed in a quantity amounting to 0.001 wt-% to 5 wt-%, in particular 0.01 wt-% to 2 wt-%, relative to the total quantity of the blend.

The silicas that are employed generally exhibit a BET surface area ($N_2$) (DIN 66131) of 60 to 700 $m^2/g$, especially with a surface area of 100 to 450 $m^2/g$.

DETAILED DESCRIPTION OF THE INVENTION

Among the suitable anti-coating agents are complexing agents that are soluble in water, such as poly(carboxylates), polyphosphonic acids, citric acid, but in particular polyacrylic acids that are obtained by homopolymerisation and alkali salts thereof, in particular sodium salts thereof, as well as maleic-acid/acrylic-acid copolymers and sodium salts thereof or mixtures thereof. They are employed in the blend in solid form in a quantity amounting to 0.05 to 4 wt-%, preferably 0.1 to 2 wt-%, relative to the total quantity of said blend.

The invention also provides the use of polyacrylic acids containing about 10% polyamide as copolymer.

The polycarboxylates that are employed include, in particular, those of the general structure (X, Y), in which X stands for

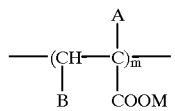

and Y stands for

with the following meanings:
A=H, OH, $C_{1-6}$ alkyl, $CH_2CO(DECO)_{r-1}OM$;
B=H, OH, $C_{1-6}$ alkyl, COOM;
D=O, NH;
E=$C_{1-6}$ alkyl, linear of branched;
F=a copolymerizable monomer;
M=H, alkali metal or alkaline-earth metal, ammonium, substituted ammonium;
in the case of X also —$(CH_2—CH_2—O)_{2-4}$M;
r=1–5;
and
m=0.5–100 mol-%
q=0–99.5 mol-%.
These compounds are known from DE-OS 4 303 320 which is relied on and incorporated herein by reference, with their use as cobuilders in washing agents.

The polycarboxylates may be used both in the form of acids and as salts or as partially neutralized substances; suitable by way of counter-ions are metal ions and also cations containing nitrogen.

The polymers having the structures (X, Y) that are employed in accordance with the invention are preferably homopolymers or copolymers of acrylic acid. The distribution of the monomers in the polymer is usually random. The copolymerisable monomer F is advantageously chosen in such a way that it does not impair the anti-coating effect of the entire polymer.

Suitable monomers F are monoethylenically unsaturated monomers that are free of carboxyl groups, such as, for example, hydroxy(meth)acrylates with $(CH_2)_xOH$ as the ester group, where x=2–4, (meth)acrylamide, (meth)acrylonitrile, vinylsulfonic acid, allylsulfonic acid, dimethylaminoethyl (meth)acrylate, diethylaminoethyl (meth)acrylate, 2-(meth)acrylamido-2-methylpropanesulfonic acid, vinylphosphonic acid, allylphosphonic acid, allyl alcohol, vinyl glycol, vinyl acetate, allyl acetate, N-vinyl pyrrolidone, N-vinyl formalize, N-vinyl imidazole, N-vinyl imidazoline, 1-vinyl-2-methyl-2-imidazoline, esters of (meth)acrylic acid with 1–8 C atoms in the alcohol residue, such as, for example, methyl (meth)acrylate, ethyl (meth)acrylate, propyl (meth)acrylate, butyl (meth)acrylate, optionally functionalized with alcohol groups or with amino groups, ethylene, propylene, methyl vinyl ether, ethyl vinyl ether, styrene and alpha-methylstyrene. All monomeric acids and bases may possibly also be used as salts.

Monomers that are multiply ethylenically unsaturated are, for example, esters formed from ethylene glycol, propylene glycol, butanediol or hexanediol with (meth)acrylic, maleic or fumaric acid, esters formed from polyethylene glycol or copolymers formed from ethylene glycol and propylene glycol with (meth)acrylic acid, maleic acid or fumaric acid, addition products of ethylene oxide and/or propylene oxide on trimethylolpropane that have been esterified two to three times with (meth)acrylic or maleic acid, at least double esters formed from (meth)acrylic or maleic acid and glycerin or pentaerythritol, triallyl amine, tetraallyl ethylenediamine, polyethylene glycol divinyl ether, trimethylolpropane diallyl ether, butanediol diallyl ether, pentaerythritol triallyl ether, divinyl urea.

Suitable for component X are monoethylenically unsaturated $C_3$ to $C_8$ monocarboxylic or dicarboxylic acids, such as, for example, acrylic acid, methacrylic acid, fumaric acid, maleic acid and also maleic anhydride, itaconic acid, citraconic acid, crotonic acid. Also suitable are the esters and amides derived from these compounds.

Also suitable are polymers that are derived from these compounds and composed of various monomeric building blocks representing structural element X.

The difference with respect to the anti-coating agent(s) that is/are present individually or jointly and the silica is made up to 100 wt-% with commercially available FAS.

It is also possible to employ carboxylic acids containing nitrogen, such as EDTA or DTPA, for example. In this case a limited effectiveness has to be reckoned with under the pH values prevailing in the bleaching liquor.

The blends are produced by known methods and can be dissolved well under practical conditions. The bleaching effect does not change in comparison with the FAS that does not contain the admixtures according to the invention.

Trials with FAS blends that contain 0.3 wt-% of a mixture of a commercially available spray-dried silica and a polyacrylic acid result in a product that is still flowable even after several months and that also exhibits the stability in storage which is striven for.

Under the operational conditions in the dissolving vessel or in the pipelines that are decisive for the assessment, no coatings were formed.

Further variations and modifications of the foregoing will be apparent to those skilled in the art and are intended to be encompassed by the claims appended hereto.

German priority applications 198 22 597.0, 198 33 629.2 and 198 53 122.2 are relied on and incorporated herein by reference.

We claim:

1. A pulverulent or granulated formamidinesulfinic acid composition having improved flow and stability properties, comprising:

formamidinesulfinic acid;

a scale-inhibiting agent comprising at least one member selected from the group consisting of a polycarboxylate, a polyphosphoric acid, and citric acid or a soluble salt thereof; and finely divided silica.

2. The composition according to claim 1, which comprises 0.05 to 4 wt-% of the scale-inhibiting agent and 0.001 to 5 wt-% of the silica, in each instance relative to the total quantity of the composition.

3. The composition according to claim 1, wherein the scale-inhibiting agent has an acidic or neutral pH value.

4. The composition according to claim 1, wherein said soluble salt is an alkali salt.

5. The composition according to claim 1, wherein the scale-inhibiting agent comprises a polyacrylic acid or a sodium salt thereof.

6. The composition according to claim 1, wherein the scale-inhibiting agent comprises a maleic-acid/acrylic-acid copolymer or a sodium salt thereof.

7. The composition according to claim 5, wherein the polyacrylic acid is comprised of about 10% of a polyamide in the form of a copolymer.

8. The composition according to claim 1, wherein the silica comprises a spray-dried precipitated silica with a specific surface area of 60 to 700 $m^2/g$ (BET, $N_2$).

9. The composition according to claim 1, wherein the scale-inhibiting agent is water soluble.

10. An aqueous composition comprising the composition of claim 1.

11. A method for the bleaching of paper or textiles, the method comprising contacting said paper of textile with the aqueous composition according to claim 10.

* * * * *